US010094767B2

(12) United States Patent
Ikuyama

(10) Patent No.: US 10,094,767 B2
(45) Date of Patent: Oct. 9, 2018

(54) IMAGE PROCESSOR, IMAGE PROCESSING METHOD, AND PROGRAM

(71) Applicant: KONICA MINOLTA, INC., Chiyoda-ku (JP)

(72) Inventor: Jun Ikuyama, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 33 days.

(21) Appl. No.: 15/510,935

(22) PCT Filed: Aug. 19, 2015

(86) PCT No.: PCT/JP2015/073184
§ 371 (c)(1),
(2) Date: Mar. 13, 2017

(87) PCT Pub. No.: WO2016/042963
PCT Pub. Date: Mar. 24, 2016

(65) Prior Publication Data
US 2017/0276598 A1 Sep. 28, 2017

(30) Foreign Application Priority Data
Sep. 19, 2014 (JP) ................. 2014-190838

(51) Int. Cl.
G06K 9/00 (2006.01)
G01N 21/27 (2006.01)
(Continued)

(52) U.S. Cl.
CPC ............. *G01N 21/27* (2013.01); *G01N 21/64* (2013.01); *G01N 21/78* (2013.01)

(58) Field of Classification Search
CPC ........... G01N 21/6456; G01N 21/6458; G06K 9/0014; G06K 9/4661; G06T 2207/10064;
(Continued)

(56) References Cited

U.S. PATENT DOCUMENTS 9,483,684 B2 * 11/2016 Tsunomori ......... G01N 21/6456
9,547,801 B2   1/2017 Marcelpoil et al.

FOREIGN PATENT DOCUMENTS

JP   2012-208106   10/2012
JP   2014-110797    6/2014
WO  WO 2013/146841 10/2013

OTHER PUBLICATIONS

International Search Report and Written Opinion dated Nov. 17, 2015 which issued in the International Patent Application No. PCT/JP2015/073184.

* cited by examiner

Primary Examiner — Manuchehr Rahmjoo
(74) Attorney, Agent, or Firm — Cozen O'Connor

(57) ABSTRACT

Image processor quantifies a specific biological material in a region of interest of a sample stained with a first staining reagent capable of staining the biological material and stained with a second staining reagent capable of staining a specific region of a cell without interfering with staining with the first staining reagent. A first input means inputs a first image showing the position of expression of the biological material stained with the first staining reagent; a second input means inputs a second image acquired in the same field of view as the first image and shows the morphology of the specific region of the cell stained with the second staining reagent; second image specific region extraction means extracts the specific region from the second image; and derivation means derives the region of interest based on at least the second image undergoing extraction of the specific region among the first and second image.

18 Claims, 12 Drawing Sheets

(51) Int. Cl.
*G01N 21/64* (2006.01)
*G01N 21/78* (2006.01)

(58) Field of Classification Search
CPC . G06T 2207/20021; G06T 2207/20104; G06T 2207/20221; G06T 2207/30024; G06T 2207/30096; G06T 7/0012
USPC .......................................................... 382/128
See application file for complete search history.

IMAGE PROCESSOR, IMAGE PROCESSING METHOD, AND PROGRAM

RELATED APPLICATIONS

This is a U.S. National Phase Application under 35 USC 371 of International Application PCT/JP2015/073184 filed on Aug. 19, 2015.

This application claims the priority of Japanese application no. 2014-190838 filed Sep. 19, 2014, the entire content of which is hereby incorporated by reference.

TECHNICAL FIELD

The present invention relates to an image processor, an image processing method, and a program.

BACKGROUND ART

In pathological diagnosis, quantification of the expression level of biological materials excessively expressed in tissue sections can provide very important information for prognostic prediction and the following treatment planning. Such quantification of biological materials involves analysis of a specific biological material in a region of interest, which is a region selected for analysis in a tissue section. For such quantification of biological materials, therefore, there has been a demand for development of techniques capable of accurately quantifying biological materials and accurately extracting a region of interest.

Thus, for example, Patent Literature 1 describes a method that includes staining tissue samples by immunohistochemical staining using a fluorescent material and analyzing the expression level of a specific protein based on the number of bright fluorescent spots in a specified region of interest. The use of a fluorescent material in immunostaining allows a specific protein to be observed as bright fluorescent dot-like spots. Therefore, this makes it possible to quantify a specific protein with high accuracy even by an immunohistochemical staining method relatively simpler than fluorescence in situ hybridization and other techniques.

CITATION LIST

Patent Literature

Patent Literature 1: WO 2013/146841 A

SUMMARY OF INVENTION

Technical Problem

In the technique described in Patent Document 1, however, the user manually selects a region of interest from an entire image and then evaluates the expression of a specific protein in the region of interest, which is laborious and can cause the problem of user-to-user variation.

In the immunohistochemical staining using a fluorescent material, the expression level of a specific protein can be measured as the brightness of the fluorescent material or as the number of bright fluorescent spots observed in the form of dots, so that the specific protein can be quantified with high accuracy. In the immunohistochemical staining using a fluorescent material, however, it is difficult to derive a region of interest from an image obtained by imaging the fluorescent material. On the other hand, DAB method, which is a dye staining method using an enzyme, allows the expression level of a specific protein to be observed as the density of the color produced by brown staining. In this method, therefore, it is relatively easy to obtain a region of interest by automatic extraction of a cell region, though the accuracy of specific protein quantification is not high. However, DAB method, which is one of immunohistochemical staining methods using an antibody to a specific protein, has a problem in that if it is used in combination with the quantification of the expression level of a specific protein in a tissue sample stained by immunohistochemical staining with a fluorescent material, it can competitively interfere with the immunohistochemical staining with the fluorescent material to make impossible accurate quantification of the fluorescent material.

An object of the present invention is to provide an image processor, an image processing method, and a program that make it possible to automatically derive, from an image of a tissue sample, a region of interest for analysis of the expression level of a specific biological material.

Solution to Problem

The present invention solves the above problems by the following means.

1. An image processor configured to quantify a specific biological material in a region of interest of a sample stained with a first staining reagent capable of staining the specific biological material and stained with a second staining reagent capable of staining a specific region of a cell without interfering with staining with the first staining reagent, the image processor including:

first input means configured to input a first image that shows a position of expression of the biological material stained with the first staining reagent;

second input means configured to input a second image that is acquired in the same field of view as the first image and shows the morphology of the specific region of the cell stained with the second staining reagent;

second image specific region extraction means configured to extract, as a second image specific region, the specific region from the second image; and derivation means configured to derive the region of interest based on at least the second image having undergone extraction of the specific region among the first image and the second image having undergone extraction of the specific region.

2. The image processor according to Item. 1, wherein the derivation means is configured to perform dilation for dilating the specific region and to derive the dilated specific region as the region of interest.

3. The image processor according to Item. 2, wherein the derivation means is configured to determine whether the specific region is necessary for derivation of the region of interest, based on the shape of the specific region, and to derive the region of interest by the dilation of the specific region that is determined to be necessary for derivation of the region of interest.

4. The image processor according to Item. 2 or 3, wherein the derivation means is configured to determine that the specific region the distance of which from another specific region closest to the specific region is at most a predetermined distance is necessary for derivation of the region of interest.

5. The image processor according to any one of Items. 2 to 4, further including density calculation means configured to calculate the density of the specific region, wherein the derivation means is configured to determine a dilation ratio for the dilation based on the density.

6. The image processor according to any one of Items. 2 to 4, further including
area calculation means configured to calculate the area of the specific region, wherein
the derivation means is configured to determine a dilation ratio for the dilation based on the area.

7. The image processor according to Item. 1, wherein the sample is a tissue section sampled from a tissue, the image processor further including:
third input means configured to input a third image that allows a region of expression of the biological material to be extracted from a consecutive sample or samples stained to allow extraction of the region of expression of the biological material and the specific region of the cell, wherein the consecutive sample or samples are a tissue section or sections consecutive to the tissue section;
consecutive sample region-of-interest extraction means configured to extract, as a consecutive sample region of interest, the region of expression of the biological material from the third image;
fourth input means configured to input a fourth image showing the morphology of the specific region in the consecutive sample or samples; and
fourth image specific region extraction means configured to extract, as a fourth image specific region, the specific region in the consecutive sample or samples from the fourth image, wherein
the derivation means is configured to derive a region of interest of the sample from the consecutive sample region of interest based on the shapes of the second image specific region and the fourth image specific region.

8. The image processor according to Item. 7, further including
correction value calculation means configured to perform pattern matching between the second image specific region and the fourth image specific region after deformation of the second image or the fourth image and to calculate, as a correction value, a deformation parameter with which the degree of matching between the second image specific region and the fourth image specific region reaches the maximum, wherein
the derivation means is configured to derive a region of interest of the sample by deforming the consecutive sample region of interest based on the correction value.

9. The image processor according to Item. 8, wherein the correction value includes a value for parallel translation and/or rotational transfer.

10. The image processor according to Item. 8 or 9, wherein the correction value includes a value for enlargement or reduction.

11. The image processor according to any one of Items. 7 to 10, wherein the consecutive samples are two tissue sections between which the sample is located.

12. The image processor according to Item. 1, wherein the derivation means is configured to derive a region of interest based on the second image having undergone extraction of the specific region and based on the first image showing the position of expression of the biological material.

13. The image processor according to Item. 12, wherein the derivation means is configured to calculate the distance from each position of expression of the biological material to the specific region closest to each position in an image obtained by superimposing the second image having undergone extraction of the specific region on the first image showing the position of expression of the biological material, and also configured to derive, as a region of interest, the inside of a contour linking outer borders of positions of expression of the biological material with the calculated distance being at most a predetermined distance.

14. The image processor according to Item. 13, wherein the predetermined distance is determined based on the size of the specific region.

15. An image processing method for quantifying a specific biological material in a region of interest of a sample stained with a first staining reagent capable of staining the specific biological material and stained with a second staining reagent capable of staining a specific region of a cell without interfering with staining with the first staining reagent, the method including:
a first input step of inputting a first image that shows the position of expression of the biological material stained with the first staining reagent;
a second input step of inputting a second image that is acquired in the same field of view as the first image and shows the morphology of the specific region of the cell stained with the second staining reagent;
a second image specific region extraction step of extracting the specific region from the second image; and
a derivation step of deriving the region of interest based on at least the second image having undergone extraction of the specific region among the first image and the second image having undergone extraction of the specific region.

16. A program for causing a computer to quantify a specific biological material in a region of interest of a sample stained with a first staining reagent capable of staining the specific biological material and stained with a second staining reagent capable of staining a specific region of a cell without interfering with staining with the first staining reagent, the program causing the computer to function as:
first input means for inputting a first image that shows the position of expression of the biological material stained with the first staining reagent;
second input means for inputting a second image that is acquired in the same field of view as the first image and shows the morphology of the specific region of the cell stained with the second staining reagent;
second image specific region extraction means for extracting the specific region from the second image; and
derivation means for deriving the region of interest based on at least the second image having undergone extraction of the specific region among the first image and the second image having undergone extraction of the specific region.

Advantageous Effects of Invention

The present invention makes it possible to automatically derive, from an image of a tissue section, a region of interest for analysis of the expression level of a specific biological material.

DESCRIPTION OF EMBODIMENTS

Hereinafter, embodiments for carrying out the present invention will be described, which, however, are not intended to limit the present invention.

<Configuration of Pathological Diagnosis Support System 100>

Figure 1:
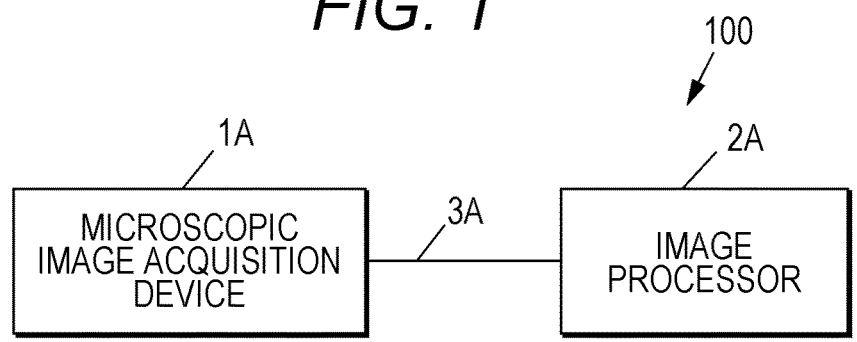
FIG. 1 is a diagram illustrating the configuration of a pathological diagnosis support system.

FIG. 1 illustrates an example of the general configuration of a pathological diagnosis support system 100 according to the embodiment. The pathological diagnosis support system 100 is configured to acquire a microscopic image of a human tissue section stained with a certain staining reagent and to output a feature value through the analysis of the acquired microscopic image, in which the feature value quantitatively indicates the expression of a specific biological material in the tissue section as an observation object.

As illustrated in FIG. 1, the pathological diagnosis support system 100 includes a microscopic image acquisition device 1A, an image processor 2A, and an interface such as a cable 3A that connects them to allow data to be sent and received between them. Any connection system may be used to connect the microscopic image acquisition device 1A and the image processor 2A. For example, the microscopic image acquisition device 1A and the image processor 2A may be connected using local area network (LAN) or wireless technology.

The microscopic image acquisition device 1A includes a known optical microscope equipped with a camera. The microscopic image acquisition device 1A is configured to acquire a microscopic image of a tissue section on a slide mounted on a slide fixing stage and to send the image to the image processor 2A. The microscopic image acquisition device 1A includes an irradiation unit, a focusing unit, an imaging unit, a communication I/F, and other components. The irradiation unit includes a light source, a filter, and other components and is configured to apply light to the tissue section on the slide mounted on the slide fixing stage. The focusing unit includes an eye lens, an object lens, and other components and is configured to focus the transmitted light, reflected light, or fluorescent light, which is generated from the tissue section on the slide when light is applied to the tissue section. The imaging unit is the camera attached to the microscope. The camera includes a charge coupled device (CCD) sensor and other components and is configured to produce digital image data for microscopic images by acquiring images that are focused on the focusing plane by the focusing unit. The communication I/F is configured to send the produced microscopic image data to the image processor 2A. In the embodiment, the microscopic image acquisition device 1A includes a bright field unit including a combination of irradiation and focusing units suitable for bright-field observation; and a fluorescence unit including a combination of irradiation and focusing units suitable for fluorescence observation. The bright-field observation and the fluorescence observation can be selected by switching between the units.

The microscopic image acquisition device 1A is not limited to a camera-equipped microscope. Alternatively, for example, the microscopic image acquisition device 1A may include a virtual microscope slide-making apparatus (see, for example, JP 2002-514319 A) configured to acquire microscopic images of the whole of a tissue section by scanning the slide on the slide fixing stage of the microscope. The virtual microscope slide-making apparatus can acquire image data that allow the whole image of the tissue section on the slide to be seen at a time on a display.

Figure 2:
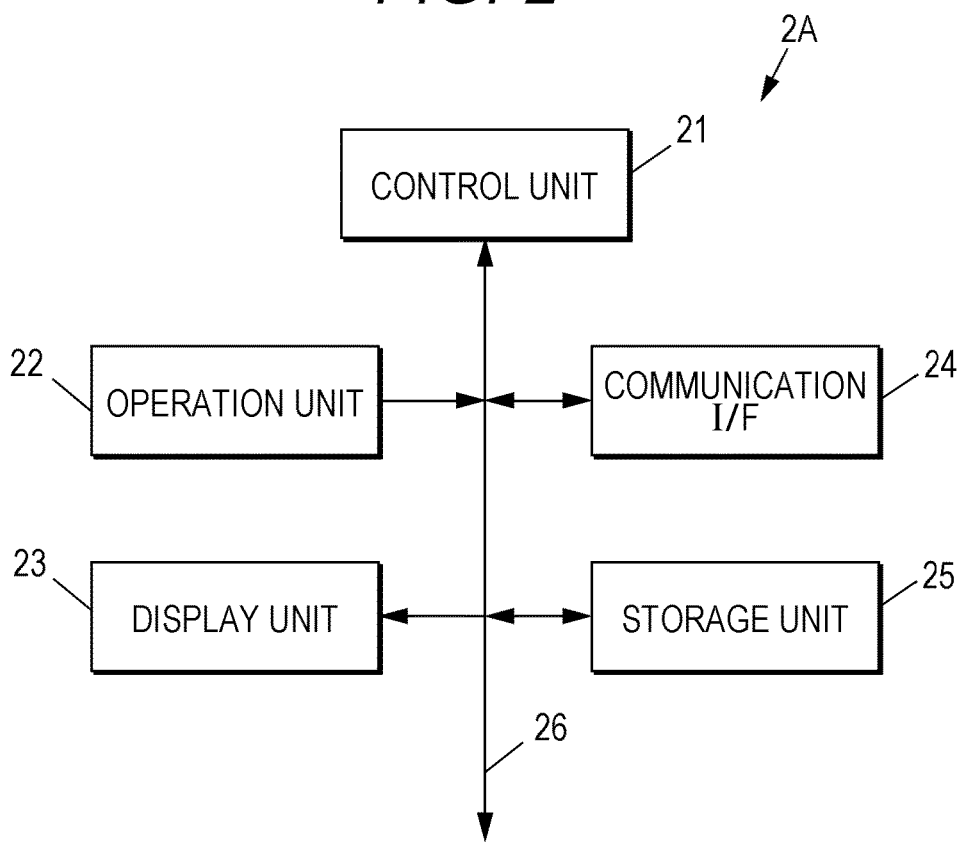
FIG. 2 is a block diagram illustrating the functional configuration of an image processor in FIG. 1.

The image processor 2A is configured to calculate a feature value through the analysis of the microscopic image sent from the microscopic image acquisition device 1A and to output the calculated feature value, in which the feature value quantitatively indicates the expression level of a specific biological material in the tissue section as an observation object. FIG. 2 illustrates an example of the functional configuration of the image processor 2A. As illustrated in FIG. 2, the image processor 2A includes a control unit 21, an operation unit 22, a display unit 23, a communication I/F 24, a storage unit 25, and other components. The individual units are connected through a bus 26.

The control unit 21 includes a central processing unit (CPU), a random access memory (RAM), and other components and is configured to execute various processes in cooperation with various programs stored in the storage unit 25 and to perform centralized control of the operation of the image processor 2A. For example, the control unit 21 is configured to execute image analysis processes (see FIGS. 5, 8, and 12) in cooperation with programs stored in the storage unit 25 and to function as means for extracting a second image specific region, derivation means, density calculation means, area calculation means, consecutive sample region-of-interest extraction means, fourth image specific region extraction means, and correction value calculation means.

The operation unit 22 includes a keyboard having character input keys, number input keys, and various function keys; and a pointing device such as a mouse, and is configured to output, as input signals to the control unit 21, signals generated by pressing keys on the keyboard and signals generated by operating the mouse.

The display unit 23 includes, for example, a monitor such as a cathode ray tube (CRT) or a liquid crystal display (LCD) and is configured to display various images on the screen according to the instructions of display signals input from the control unit 21. In the embodiment, the display unit 23 functions as means for outputting the calculated feature value.

The communication I/F 24 is an interface configured to send and receive data to and from external apparatuses including the microscopic image acquisition device 1A. The communication I/F 24 functions as first, second, third, and fourth input means.

The storage unit 25 includes, for example, a hard disk drive (HDD) or a nonvolatile semiconductor memory. As mentioned above, various programs and data are stored in the storage unit 25. For example, various data including a magnification table 251 for use in the image analysis process described later are stored in the storage unit 25. Besides the above, the image processor 2A may include a LAN adapter, a router, and other components, and be configured to be connected with external apparatuses through a communication network such as a LAN.

In the embodiment, the image processor 2A is configured to perform analysis using a bright field image (HE-stained image) and a fluorescence image, which are sent from the microscopic image acquisition device 1A. The bright field image is a microscopic image obtained by enlarging, focusing, and capturing, in the bright field of the microscopic image acquisition device 1A, an image of a tissue section stained by hematoxylin-eosin (HE) staining and/or DAB staining.

Figure 3:
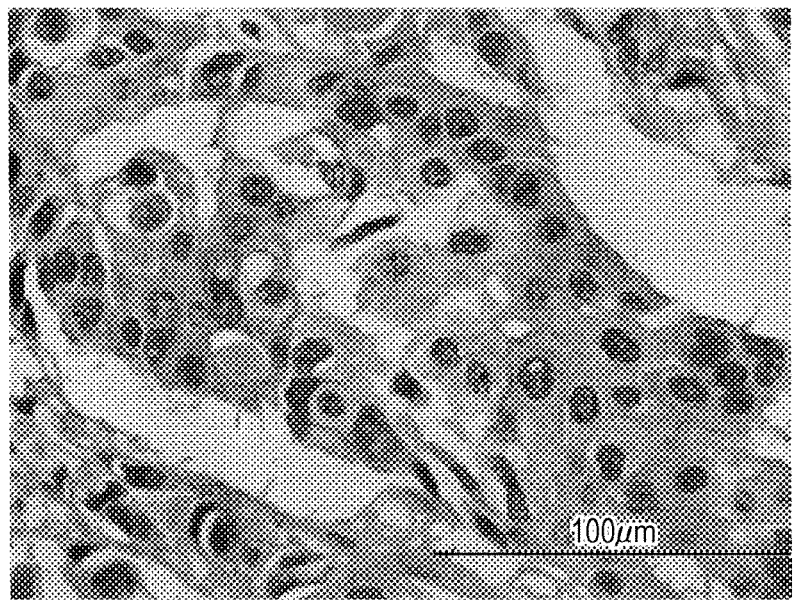
FIG. 3 is a view showing an example of a bright field image.

Hematoxylin is a blue-purple dye capable of staining, for example, cell nuclei, bone tissues, part of cartilage tissue, and serum components (basophilic tissues and other components). Eosin is a red or pink dye capable of staining, for example, cytoplasm, connective tissues in soft tissues, erythrocytes, fibrin, and endocrine granules (acidophilic tissues and other components). FIG. 3 shows an example of a bright field image acquired of a HE-stained tissue section. FIG. 3 shows that the bright field image acquired of a HE-stained tissue section shows the morphology of cells in the tissue section. The cell nuclei are shown with a color (blue-purple) darker than that of the surrounding cytoplasm, and thus distinguishable from the surrounding. In the bright field image, the morphology of cell nuclei can be clearly observed. In the DAB staining, an antigen (biological material to be observed) is stained by color development with an antibody that is modified with a peroxidase capable of producing brown color development when diaminobenzidine (DAB) is used as a substrate.

Figure 4:
FIG. 4 is a view showing an example of a fluorescence image.

The fluorescence image is a microscopic image obtained by a process that includes applying, in the microscopic image acquisition device 1A, exciting light with a predetermined wavelength to a tissue section stained with a staining reagent containing a fluorescent material to which a biological material-recognizing component capable of specifically binding to and/or reacting with a specific biological material is bonded, so that light (fluorescence) is emitted from the fluorescent material; and magnifying, focusing, and imaging the fluorescence. Therefore, the fluorescence observed in the fluorescence image indicates the expression of the specific biological material corresponding to the biological material-recognizing component in the tissue section. FIG. 4 shows an example of the fluorescence image.

<Method for Acquiring Fluorescence Image>

Hereinafter, methods for acquiring fluorescence images will be described in detail, together with staining reagents (fluorescent material-containing nanoparticles) for use in acquiring the fluorescence images, methods for staining tissue sections with the staining reagents, and other techniques.

[Fluorescent Material]

Examples of fluorescent materials for use in staining reagents for acquiring fluorescence images include fluorescent organic dyes and quantum dots (semiconductor particles). The fluorescent materials are preferably capable of emitting visible to near-infrared light with a wavelength in the range of 400 to 1,100 nm when excited with ultraviolet to near-infrared light with a wavelength in the range of 200 to 700 nm.

Examples of fluorescent organic dyes include fluorescein dye molecules, rhodamine dye molecules, Alexa Fluor (manufactured by Invitrogen Corporation) dye molecules, BODIPY (manufactured by Invitrogen Corporation) dye molecules, cascade dye molecules, coumarin dye molecules, eosin dye molecules, NBD dye molecules, pyrene dye molecules, Texas Red dye molecules, and cyanine dye molecules.

Specific examples include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, and BODIPY 650/665 (all manufactured by Invitrogen Corporation), methoxycoumarin, eosin, NBD, pyrene, Cy5, Cy5.5, and Cy7. These may be used alone or in mixture of two or more.

The quantum dots may be either quantum dots including a group II-VI compound as a component, quantum dots including a group III-V compound as a component, or quantum dots including a group IV element as a component (also referred to as "group II-VI quantum dots", "group III-V quantum dots," or "group IV quantum dots," respectively). Quantum dots of one of these types may be used, or a mixture of quantum dots of two or more of these types may be used.

Specific examples include, but are not limited to, CdSe, CdS, CdTe, ZnSe, ZnS, ZnTe, InP, InN, InAs, InGaP, GaP, GaAs, Si, and Ge.

Quantum dots each including a quantum dot core and a shell thereon may also be used. In the description, hereinafter, CdSe/ZnS will be used as a notation for shell-coated quantum dots in which the core is CdSe and the shell is ZnS. Examples of shell-coated quantum dots that may be used include, but are not limited to, CdSe/ZnS, CdS/ZnS, InP/ZnS, InGaP/ZnS, Si/SiO$_2$, Si/ZnS, Ge/GeO$_2$, and Ge/ZnS. If necessary, quantum dots surface-treated with an organic polymer or other materials may also be used. Such quantum dots include, for example, CdSe/ZnS having carboxy groups on the surface (manufactured by Invitrogen Corporation) and CdSe/ZnS having amino groups on the surface (manufactured by Invitrogen Corporation).

[Fluorescent Material-Containing Nanoparticles]

It is preferred that the fluorescent material should form nanoparticles containing the fluorescent material (called fluorescent material-containing nanoparticles), because using the fluorescent material-containing nanoparticles, the expression level of a specific biological material can be calculated not only as the brightness of fluorescent particles but also as the number of particles, which can provide high quantification accuracy. In the embodiment, the fluorescent material-containing nanoparticles refer to nanoparticles containing the fluorescent material dispersed therein, in which the fluorescent material may be chemically bonded to the nanoparticles themselves, but it is not necessary. The nanoparticles may be made of any material, such as polystyrene, polylactic acid, or silica.

The fluorescent material-containing nanoparticles used in the embodiment can be produced by a known method. For example, fluorescent organic dye-containing silica nanoparticles can be synthesized with reference to the synthesis of FITC-containing silica particles described in Langmuir, Vol. 8, p. 2921 (1992). Different types of fluorescent organic dye-containing silica nanoparticles can be synthesized using desired fluorescent organic dyes in place of FITC.

Quantum dot-containing silica nanoparticles can be synthesized with reference to the synthesis of CdTe-containing silica nanoparticles described in New Journal of Chemistry, Vol. 33, p. 561 (2009).

Fluorescent organic dye-containing polystyrene nanoparticles can be produced by the copolymerization method described in U.S. Pat. No. 4,326,008 (1982) using a polymerizable functional group-containing organic dye or by the method described in U.S. Pat. No. 5,326,692 (1992) for impregnating polystyrene nanoparticles with a fluorescent organic dye.

Quantum dot-containing polymer nanoparticles can be produced using the method described in Nature Biotechnology, Vol. 19, p. 631 (2001) for impregnating polystyrene nanoparticles with quantum dots.

The average particle size of the fluorescent material-containing nanoparticles for use in the embodiment may be, but not limited to, about 30 to about 800 nm. The coefficient of variation (=(standard deviation/average)×100%), which is a measure of variations in particle size, is preferably, but is not limited to, 20% or less. The average particle size was determined as follows. An electron micrograph was taken using a scanning electron microscope (SEM). The cross-sectional areas of a sufficient number of particles were measured in the micrograph, and assuming that each measured value was the area of a circle, the particle size was calculated as the diameter of the circle. In the present disclosure, the average particle size was defined as the arithmetic mean of the particle sizes of 1,000 particles. The coefficient of variation was also calculated from the particle size distribution of 1,000 particles.

[Bonding Between Biological Material-Recognizing Component and Fluorescent Material-Containing Nanoparticles]

In the embodiment, the biological material-recognizing component refers to a component capable of specifically binding to and/or reacting with a target biological material. The target biological material may be of any type as long as a substance capable of specifically binding to it exists. Typical examples of the target biological material include proteins (peptides), nucleic acids (oligonucleotides and polynucleotides), and antibodies. Therefore, examples of the material capable of binding to such examples of the target biological material include antibodies capable of recognizing the above proteins as antigens, other proteins capable of specifically binding to the above proteins, and nucleic acids having base sequences capable of hybridizing to the above nucleic acids. Specific examples include anti-HER2 antibodies capable of specifically binding to HER2 (a protein present on the surface of cells), anti-ER antibodies capable of specifically binding to the estrogen receptor (ER) present in cell nuclei, and anti-actin antibodies capable of specifically binding to actin, which forms the cytoskeleton. Particularly preferred are products obtained by bonding an anti-HER2 antibody to fluorescent material-containing nanoparticles and products obtained by bonding an anti-ER antibody to fluorescent material-containing nanoparticles, which can be used for selection of the drug to be administered for breast cancer.

The biological material-recognizing component and the fluorescent material-containing nanoparticles may be bonded in any manner. Examples of the bonding include covalent bonding, ionic bonding, hydrogen bonding, coordinate bonding, physical adsorption, and chemical adsorption. In view of bonding stability, high-strength bonding is preferred, such as covalent bonding.

An organic molecule may also be provided to link the biological material-recognizing component to the fluorescent material-containing nanoparticle. For example, to suppress nonspecific adsorption to the biological material, a polyethylene glycol chain, such as SM(PEG)12 manufactured by Thermo Fisher Scientific Inc., may be used as such an organic molecule.

Similar procedures may be used to bond the biological material-recognizing component to fluorescent material-containing silica nanoparticles regardless of whether the fluorescent material is a fluorescent organic dye or a quantum dot. For example, a silane coupling agent may be used, which is a compound widely used to bond organic materials to inorganic materials. Such a silane coupling agent is a compound having an alkoxysilyl group, which can give rise to a silanol group upon hydrolysis, at one molecular end and having a functional group such as a carboxyl, amino, epoxy, or aldehyde group at the other end. Such a silane coupling agent can be bonded to inorganic materials through the oxygen atom of the silanol group. Specific examples of the silane coupling agent include mercaptopropyltriethoxysilane, glycidoxypropyltriethoxysilane, aminopropyltriethoxysilane, and polyethylene glycol chain-containing silane coupling agents (such as PEG-silane no. SIM6492.7 manufactured by Gelest, Inc.). Two or more silane coupling agents may be used in combination.

A known technique may be used in the procedure for the reaction of the fluorescent organic dye-containing silica nanoparticles with the silane coupling agent. For example, the resulting fluorescent organic dye-containing silica nanoparticles are dispersed in pure water, and aminopropyltriethoxysilane is added to the dispersion and allowed to react at room temperature for 12 hours. After the reaction is completed, fluorescent organic dye-containing silica nanoparticles with their surface modified with an aminopropyl group are obtained by centrifugation or filtration of the reaction product. Subsequently, the amino group is allowed to react with a carboxyl group of an antibody, so that the antibody is bonded to the fluorescent organic dye-containing silica nanoparticle through an amide bond. If necessary, a condensing agent may also be used, such as 1-ethyl-3-[3-dimethylaminopropyl]carbodiimide hydrochloride (EDC) (manufactured by Pierce (registered trademark)).

If necessary, a linker compound having a moiety capable of being bonded directly to the fluorescent organic dye-containing silica nanoparticles modified with the organic molecule and having another moiety capable of being bonded to the molecular target material may be used. As a specific example, sulfosuccinimidyl 4[N-maleimidomethyl]-cyclohexane-1-carboxylate (sulfo-SMCC) (manufactured by Pierce) may be used, which has both a moiety capable of selectively reacting with an amino group and a moiety capable of selectively reacting with a mercapto group. In this case, using this compound, antibody-coupled, fluorescent organic dye-containing, silica nanoparticles can be produced by bonding a mercapto group of an antibody to an amino group of each of fluorescent organic dye-containing silica nanoparticles modified with aminopropyltriethoxysilane.

Similar procedures may be used to bond the biological material-recognizing component to fluorescent material-containing polystyrene nanoparticles regardless of whether the fluorescent material is a fluorescent organic dye or a quantum dot. Specifically, polystyrene nanoparticles having a functional group such as an amino group may be impregnated with a fluorescent organic dye or a quantum dot to form fluorescent material-containing polystyrene nanoparticles having the functional group. Subsequently, antibody-coupled, fluorescent material-containing, polystyrene nanoparticles can be produced using EDC or sulfo-SMCC.

Non-limiting examples of the biological material-recognizing component include M. actin, M.S. actin, S.M. actin, ACTH, Alk-1, α1-antichymotrypsin, α1-antitrypsin, AFP, bcl-2, bcl-6, β-catenin, BCA225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, CD99, MIC2, CD138, chromogranin, c-KIT, c-MET, collagen type IV, Cox-2, cyclin D1, keratin, cytokeratin (high molecular weight), pan-keratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, factor VIII-related antigen, fassin, FSH, galectin-3, gastrin, GFAP, glucagon, glycophorin A, granzyme B, hCG, hGH, *Helicobacter pyroli*, HBc antigen, HBs antigen, hepatocyte-specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kip1), p53, p53, P63, PAX5, PLAP, *Pneumocystis calini*, podoplanin (D2-40), PGR, prolactin, PSA, prostatic acid phosphatase, renal cell carcinoma, S100, somatostatin, spectrin, synaptophysin, TAG-72, TdT, cycloglobulin, TSH, TTF-1, TRAcP, tryptase, villin, vimentin, WT1, Zap-70, and other specific antigen-recognizing antibodies.

[Staining Method]

Hereinafter, a tissue section-staining method will be described. The staining method described below can be used to stain not only pathological tissue sections but also cells. Sections prepared by any known method may be used in the staining method described below.

(1) Deparaffinization Step

A pathological section is immersed in xylene in a vessel so that paraffin is removed from the section. The deparaffinization temperature may be, but not limited to, room temperature. The immersion time is preferably from 3 minutes to 30 minutes. If necessary, the used xylene may be replaced with fresh xylene during the immersion. The pathological section is then immersed in ethanol in a vessel so that xylene is removed from the section. The removal temperature may be, but not limited to, room temperature. The immersion time is preferably from 3 minutes to 30 minutes. If necessary, the used ethanol may be replaced with fresh ethanol during the immersion. The pathological section is then immersed in water in a vessel so that ethanol is removed from the section. The deparaffinization temperature may be, but not limited to, room temperature. The immersion time is preferably from 3 minutes to 30 minutes. If necessary, the used water may be replaced with fresh water during the immersion.

(2) Activation Treatment

According to a known method, the target biological material is subjected to an activation treatment. The activation may be performed under any conditions. Examples of activation solutions that may be used include a 0.01 M citric acid buffer (pH 6.0), a 1 mM EDTA solution (pH 8.0), 5% urea, and a 0.1 M Tris hydrochloride buffer. Examples of heating devices that may be used include autoclaves, microwave ovens, pressure cookers, and water baths. The activation temperature may be, but not limited to, room temperature. The activation may be performed at a temperature of 50 to 130° C. for a time period of 5 to 30 minutes. Subsequently, the section after the activation treatment is cleaned by immersion in phosphate buffered saline (PBS) in a vessel. The cleaning temperature may be, but not limited to, room temperature. The immersion time is preferably from 3 minutes to 30 minutes. If necessary, the used PBS may be replaced with fresh PBS during the immersion.

(3) A PBS dispersion of the fluorescent material-containing nanoparticles a staining biological material-recognizing component bonded thereto is placed on the pathological section and allowed to react with the target biological material, the staining biological material-recognizing component using the fluorescent material-containing nanoparticles with the biological material-recognizing component bonded thereto (a first staining reagent). The staining is made applicable to various biological materials by changing the biological material-recognizing component to be bonded to the fluorescent material-containing nanoparticles. Fluorescent material-containing nanoparticles with several biological material-recognizing components bonded thereto may also be used. In this case, PBS dispersions of respective types of fluorescent material-containing nanoparticles may be mixed in advance or may be separately and sequentially placed on the pathological section. The reaction temperature may be, but not limited to, room temperature. The reaction time is preferably from 30 minutes to 24 hours. A known blocking agent such as BSA-containing PBS is preferably added dropwise before the staining with the fluorescent material-containing nanoparticles.

Subsequently, the section after the staining is immersed in PBS in a vessel so that the unreacted fluorescent material-containing nanoparticles are removed. The immersion temperature may be, but not limited to, room temperature. The immersion time is preferably from 3 minutes to 30 minutes. If necessary, the used PBS may be replaced with fresh PBS during the immersion. A cover glass is placed over the section and then sealed. If necessary, a commercially available mounting agent may also be used. For example, when HE staining is performed as staining with a second staining reagent, it should be performed before the sealing with the cover glass. The staining with the second staining reagent may be performed using any staining method that does not interfere with the staining method for quantifying the specific protein. For example, when immunohistochemical staining with a fluorescent dye is performed as the staining method for quantifying the specific protein, an HE staining reagent is preferably used as the second staining reagent to stain cell nuclei.

[Acquiring Fluorescence Image]

A wide-field, microscopic image (fluorescence image) of the stained pathological section is acquired using the microscopic image acquisition device 1A. In the microscopic image acquisition device 1A, the exciting light source and the optical filter for fluorescence detection are selected depending on the absorption maximum wavelength of the fluorescent material used in the staining reagent and the fluorescence wavelength. The fluorescence image field is preferably 3 mm$^2$ or more, more preferably 30 mm$^2$ or more, even more preferably 300 mm$^2$ or more.

<Operation of Pathological Diagnosis Support System 100>

Hereinafter, a description will be given of the operation of the pathological diagnosis support system 100 in which the fluorescence image and the bright field image described above are acquired and analyzed. Hereinafter, a non-limiting example will be described, in which the specific biological material is a specific protein (in this case, HER2 protein (hereinafter referred to as the specific protein) in breast cancer tissues), the observation object is a tissue section stained with a staining reagent containing fluorescent material-containing nanoparticles to which a biological material-recognizing component capable of recognizing the specific protein is bonded, and a region of interest is derived from regions surrounded by the cell membrane on which the HER2 protein is expressed.

[Process of Deriving First Region of Interest]

In the process of deriving a first region of interest, the image processor 2A derives a region of interest, based on nuclear regions (specific regions) that are extracted based on HE staining (staining with a second staining reagent).

Firstly, using the microscopic image acquisition device 1A, the operator acquires a bright field image (second image) and a fluorescence image (first image) by the procedures (a1) to (a5). (a1) A slide on which a tissue section is mounted is placed on the slide fixing stage of the microscopic image acquisition device 1A, in which the tissue section has been stained with an HE staining reagent and a staining reagent including, as a fluorescent label material, the fluorescent material-containing nanoparticles to which the biological material-recognizing component capable of recognizing the specific protein has been bonded. (a2) The bright field unit is selected, in which the imaging magnification and the focusing are controlled so that the region of the object to be observed on the tissue is placed in the field of view. (a3) Bright field image data are produced by imaging with the imaging unit and then sent to the image processor 2A. (a4) The unit is changed to the fluorescence unit. (a5) Fluorescence image data are produced by imaging with the imaging unit without changing the field of view and the imaging magnification and then sent to the image processor 2A.

In this way, the bright field image and the fluorescence image are acquired in the same area (the same field of view) at the same imaging magnification from the same tissue section on the slide in the microscopic image acquisition device 1A. Therefore, the same coordinates on the bright field image and the fluorescence image indicate the same positions on the tissue section, which eliminates the need for controlling the positions of both images.

In this case, the microscope used was an upright microscope BX53 manufactured by Olympus Corporation, in which a 40× objective lens was selected and used to focus the fluorescence emitted from the tissue section irradiated with the exciting light. The fluorescence image (image data) was acquired by the camera (color) attached to the microscope and then input into the image processor 2A in which image analysis software is used to count the number of bright fluorescent spots. The camera has a pixel size of 4.4 µm×4.4 µm, a number of vertical pixels of 1,200, and a number of horizontal pixels of 1,600 (imaging region 7.2 mm×5.3 mm).

The inventors' study has demonstrated that the bright fluorescent spots can be automatically detected from the microscopic image (fluorescence image) in both of an 8-bit processing system (0 to 255 scale) and a 12-bit processing system (0 to 4,095 scale) if the bright fluorescent spots of the fluorescent material-containing nanoparticles differ in the amount of emitted light by 10% (1.1 times) or more from the self-fluorescence of the tissue and the eosin emission (background) when HE staining and staining with the fluorescent material-containing nanoparticles are performed at the same time. The inventors' study has also demonstrated that the bright fluorescent spots can be automatically detected in both of an 8-bit processing system (0 to 255 scale) and a 12-bit processing system (0 to 4,095 scale) if the bright fluorescent spots of the fluorescent material-containing nanoparticles differ in the amount of emitted light by 10% (1.1 times) or more from the self-fluorescence of the tissue when only the fluorescent material-containing nanoparticles are used for staining. In the fluorescence unit, therefore, the wavelength of the exciting light is preferably selected to be in the range of 560 to 630 nm. The fluorescent material used preferably emits fluorescence with a peak at a wavelength in the range of 580 to 690 nm, more preferably in the range of 600 to 630 nm, when irradiated with the exciting light. This is because when the exciting light in the above range is selected, the use of the fluorescent material having a peak in this range can ensure a significant difference between the self-fluorescence of the tissue (including the eosin emission) and the fluorescence from the fluorescent material-containing nanoparticles (a difference of 10% (1.1 times) or more in the amount of light between them), so that they can be distinguished and recognized. In the embodiment, the 8-bit processing system is used.

Figure 5:
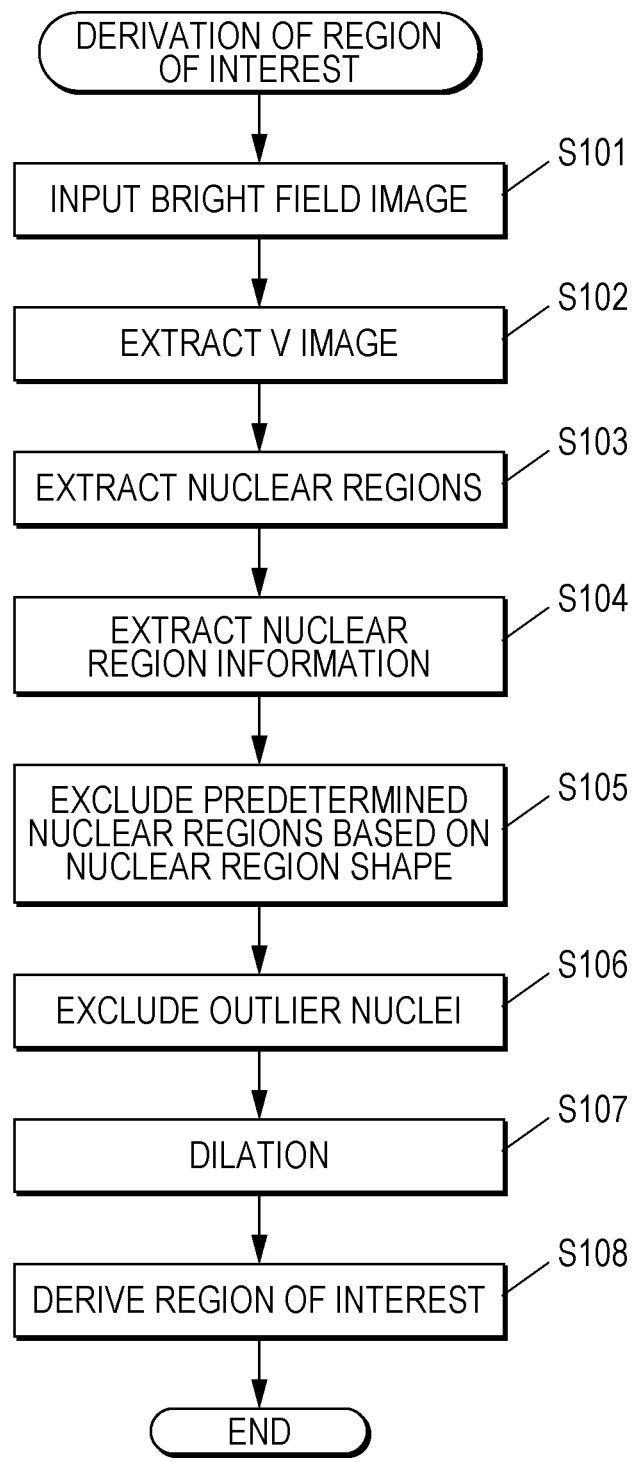
FIG. 5 is a flowchart illustrating a process of deriving a first region of interest, which is executed by a control unit illustrated in FIG. 2.

FIG. 5 is a flowchart illustrating the process of deriving a first region of interest in the embodiment. The process of deriving a first region of interest is executed by cooperation of the control unit 21 and programs stored in the storage unit 25.

Figure 6A:
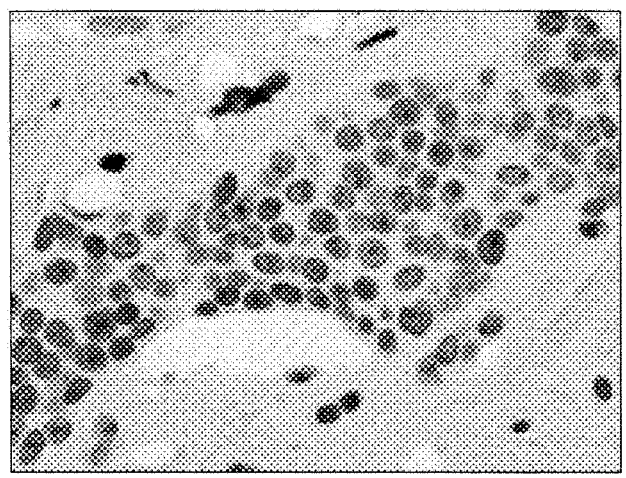
FIG. 6A is a view showing an example of image processing in steps S102 to S105 of FIG. 5.

Firstly, the bright field image (second image) is input from the microscopic image acquisition device 1A through the communication I/F 24 (step S101 (second input step)). The bright field image is then subjected to normalization and HSV decomposition so that the V image is extracted as a result of the extraction of the brightness component from the bright field image (step S102). Subsequently, cell nuclear regions (nuclear regions or second image specific regions) are extracted from the V image (step S103 (the step of extracting second image specific regions)). Any method may be used to extract nuclear regions from the V image. For example, each pixel value in the V image obtained as a monochrome image by conversion as shown in FIG. 6A is binarized using a predetermined threshold. In this regard, the threshold is appropriately changed depending on the image acquiring conditions, the staining method, the tissue section thickness, or other factors.

Figure 6B:
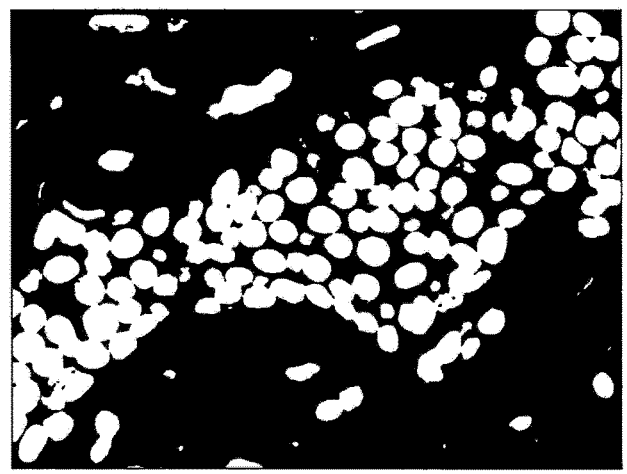
FIG. 6B is a view showing an example of image processing in steps S102 to S105 of FIG. 5.

In step S103, noise processing is further performed. Specifically, the noise processing may be performed by closing the binary image. The closing includes performing dilation a certain number of times and then performing erosion the same number of times. The dilation is a process in which if there is at least one white pixel in an n×n pixel area (n is an integer of 2 or more) from a notice pixel, the notice pixel is replaced with a white pixel. The erosion is a process in which if there is at least one black pixel in an n×n pixel area from a notice pixel, the notice pixel is replaced with a black pixel. The closing can remove small regions such as noise. FIG. 6B shows an image obtained by binarizing the image of FIG. 6A with an intensity threshold of 200 and then reversing black and white. An image having nuclear regions extracted based on the HE staining (a nuclear region image) is obtained by the processing of step S103.

After the noise processing, the image is subjected to labeling in which a label is attached to each of the extracted nuclear regions. The labeling is a process in which the same label (number) is attached to connected pixels to identify objects in the image. The labeling makes it possible to identify each nuclear region from the image after the noise processing and to attach a label to each nuclear region.

Subsequently, information is extracted about each of the extracted nuclear regions (step S104). Information about each nuclear region is any pieces of information about the morphological feature values of each nuclear region. Examples of such information include the length (long diameter), width (short diameter), and area of the nuclear region, the distance from the adjacent nuclear region, and the density of the nuclear region in a predetermined area from the center of gravity of the nuclear region.

Subsequently, the processing of steps S105 to S108 is performed so that a region of interest is derived by excluding, from the nuclear region image, nuclear regions not satisfying predetermined conditions. Any predetermined conditions may be selected depending on the type of the tissue sample and the specific protein, the region of interest to be derived, or other factors. Hereinafter, an example will be described in which a region having a plurality of cells packed densely is derived as a region of interest.

Figure 6C:
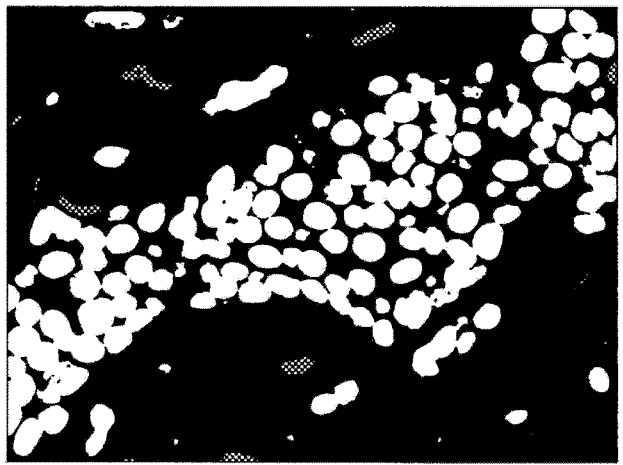
FIG. 6C is a view showing an example of image processing in steps S102 to S105 of FIG. 5.

Firstly, nuclear regions having a predetermined shape feature are excluded from the nuclear region image (step S105). Specifically, in the nuclear region image of FIG. 6B, for example, when the average area of the nuclear regions is 3,000 pixels, slender regions having an area of 5,000 pixels or less and a main axis length/maximum main width ratio of 2 or more are determined to be unnecessary for the derivation of a region of interest and thus excluded, because they should be non-nuclear noise. Even when having a main axis length/maximum main width ratio of 2 or more, nuclear regions having an area of more than 5,000 pixels are determined to be necessary for the derivation of a region of interest and thus not excluded, because they should be regions having a plurality of cell nuclei overlapping one another. FIG. 6C is an exemplary image in which the regions to be excluded from FIG. 6B by the processing of step S105 are indicated in gray. In this regard, the main axis length of the nuclear region refers to the length of the long diameter of the nuclear region, and the maximum main width refers to the maximum value of the length of the nuclear region in the direction perpendicular to the main axis.

Figure 7A:
FIG. 7A is a view showing an example of image processing in steps S106 to S108 of FIG. 5.

Subsequently, nuclear regions the distance of which from the most adjacent nuclear region is equal to or more than a predetermined value are excluded as being outlier nuclei distant from other cell nuclei (step S106). In other words, if there are other specific regions within the predetermined distance, such specific regions will be determined to be necessary for the derivation of a region of interest, because it is suggested that there should be densely packed cells in the vicinity of such specific regions. The distance between nuclear regions may be freely defined. For example, the distance between nuclear regions may be defined as the distance between the centers of gravity of nuclear regions or as the minimum value of the length of a line between any points on the contours of nuclear regions. Any predetermined value may be selected based on the type of the tissue sample and the average diameter of nuclear regions. The diameter of the nuclear region may be freely defined. For example, the diameter of the nuclear region may be defined as the diameter of a circle having the same area as the calculated area of the nuclear region. For example, the nuclear regions shown in FIG. 6B have an average diameter of 50 pixels, and FIG. 7A shows an image obtained by excluding, from the image of FIG. 6C, nuclear regions the distance of which from the most adjacent nuclear region is more than 1.2 times (60 pixels) the average diameter of the nuclear regions, which are determined to be outlier nuclei.

Figure 7B:
FIG. 7B is a view showing an example of image processing in steps S106 to S108 of FIG. 5.

Subsequently, the nuclear regions that are determined to be necessary for the derivation of a region of interest are subjected to dilation (step S107). In the dilation, the unsmoothed image is added to the image having undergone smoothing in which each pixel in the image is replaced with the average of the pixels in an n×n pixel area (n is an integer of 2 or more) from a notice pixel, so that an image with the contours of the nuclear regions blurred is obtained. The dilation ratio (the size of the pixels subjected to dilation and the number of times of dilation) may be selected freely. For example, FIG. 7B shows an image obtained by dilation of the image of FIG. 7A, in which a process including performing smoothing on a 101×101 pixel area and then adding the unsmoothed image to the smoothed image is repeated five times.

Figure 7C:
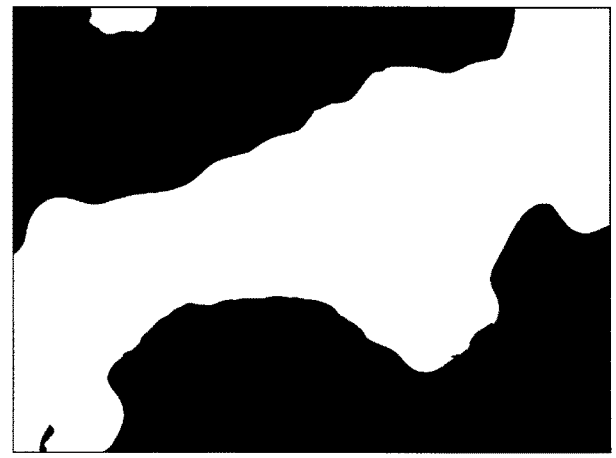
FIG. 7C is a view showing an example of image processing in steps S106 to S108 of FIG. 5.

In step S108, each pixel value of the image obtained by the dilation in step S107 is binarized with a predetermined threshold so that a binary image of the dilated nuclear regions is obtained. In step S108, a region of interest is derived by further excluding very small regions that are determined not to be regions having a plurality of nuclear regions packed densely. FIG. 7C shows an image obtained by a process that includes binarizing the image of FIG. 7B with an intensity threshold of 127 and further excluding very small regions with an area of 5,000 pixels or less so that a region having a plurality of nuclear regions packed densely is derived as a region of interest.

The size of the pixels subjected to the smoothing in step S107 is preferably determined according to the definition of the outlier nuclei to be excluded in step S106. For example, in the image of FIG. 7A, nuclear regions the distance of which from the most adjacent nuclear region is more than 1.2 times (60 pixels) the average diameter of the nuclear regions are excluded as outlier nuclei, and smoothing is performed on a 101×101 pixel area, which is about twice the average diameter of the nuclear regions, so that the intensity is increased in the area between adjacent nuclear regions. Subsequently, binarization with a suitable threshold is performed in step S108, so that a region covering adjacent nuclear regions is derived as a region of interest.

The dilation in step S107 may include the step of calculating the area of the nuclear regions (the area calculation step) or the step of calculating the density of the nuclear regions (the number of nuclear regions per area) (the density calculation step), and the dilation ratio may be determined based on the calculation. For example, even when the tissue has a low cell density and a small nuclear region area or density, the use of a large dilation ratio makes it possible to derive, as a region of interest, a single region formed by collecting regions in which a plurality of cells are packed in a relatively high density.

The control unit 21 analyzes the number of bright fluorescent spots in the region of interest derived by the processing described above and evaluates the expression of the specific protein.

[Process of Deriving Second Region of Interest]

In general, two tissue sections consecutively obtained from a tissue sample have no significant difference in tissue morphology. Therefore, regions of interest from two tissue sections can be assumed to substantially coincide with each other when the positions of the images of the two tissue sections are corrected. Therefore, in the process of deriving a second region of interest, the image processor 2A derives regions of interest, for example, from tissue sections consecutively obtained for observation and quantification of a specific protein, based on the staining of the specific protein by an immunohistochemical staining method such as a DAB method. The positions and shapes of the regions of interest derived from the consecutive samples are then corrected based on a mismatch between the HE-stained images of the two tissue sections, so that a region of interest is determined for the tissue sections observed.

Hereinafter, the process of deriving a second region of interest will be described mainly with respect to its features different from those of the process of deriving the first region of interest, while a description of common features will be omitted. Firstly, using the microscopic image acquisition device 1A, the operator acquires bright field images and fluorescence images by the procedures (b1) to (b7). (b1) Two consecutive tissue sections (section A (a sample) and section B (a consecutive sample)) are prepared. Section A is then stained with a staining reagent including, as a fluorescent label material, the fluorescent material-containing nanoparticles to which the biological material-recognizing component capable of recognizing the specific protein is bonded (first staining reagent) and stained with an HE staining reagent (second staining reagent). Subsequently, the specific protein in section B is stained by a DAB method and further stained with an HE staining reagent. (b2) A slide on which section A is mounted is placed on the slide fixing stage of the microscopic image acquisition device 1A. The bright field unit is selected, in which the imaging magnification and the focusing are controlled so that the region of the object to be observed on the tissue is placed in the field of view. (b3) Bright field image (second image) data of section A are produced by imaging with the imaging unit and then sent to the image processor 2A. (b4) The unit is changed to the fluorescence unit. (b5) Fluorescence image (first image) data of section A are produced by imaging with the imaging unit without changing the field of view and the imaging magnification and then sent to the image processor 2A. (b6) A slide on which section B is mounted is placed on the slide fixing stage of the microscopic image acquisition device 1A. The bright field unit is selected, in which the imaging magnification is the same as that in the procedure (b2) and the focusing is controlled so that a region substantially adjacent to the observed region of section A imaged in the procedure (b2) is placed in the field of view. (b7) Data about bright field images (third and fourth images) of section B are produced by imaging with the imaging unit and then sent to the image processor 2A.

In this way, the bright field image and the fluorescence image are acquired in the same area (same field of view) at the same imaging magnification from section A mounted on the slide in the microscopic image acquisition device 1A. Therefore, the same coordinates on the bright field image and the fluorescence image of section A indicate the same positions on the tissue section, which eliminates the need for alignment of both images.

Figure 8:
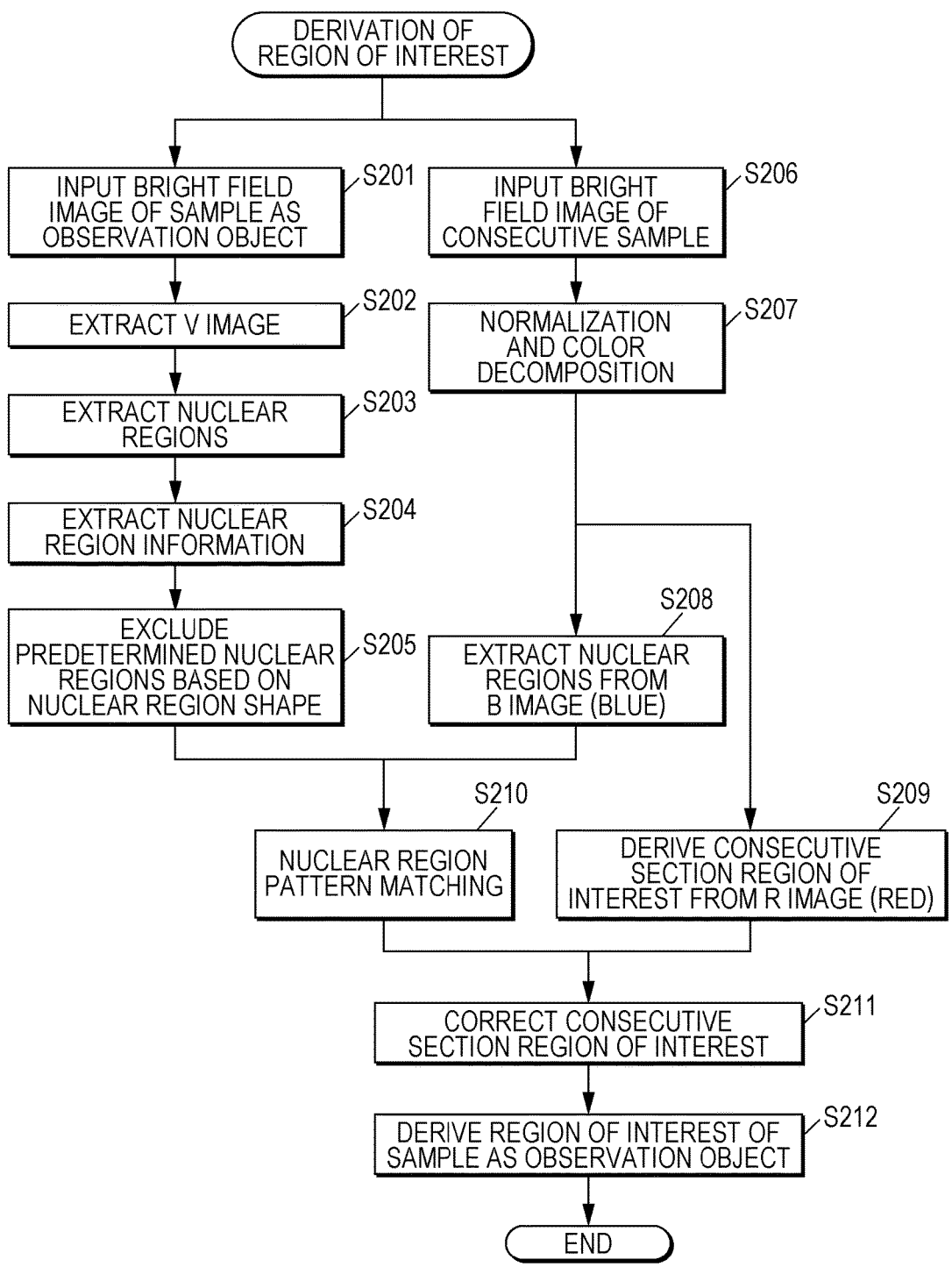
FIG. 8 is a flowchart illustrating a process of deriving a second region of interest, which is executed by the control unit shown in FIG. 2.

FIG. 8 is a flowchart illustrating the process of deriving a second region of interest in the embodiment. The second image analysis is executed by cooperation of the control unit 21 and programs stored in the storage unit 25.

Firstly, the bright field image of section A as an observation object is input from the microscopic image acquisition device 1A through the communication I/F 24 (step S201 (second input step)). The bright field image is then subjected to normalization and HSV decomposition so that the V image is extracted (step S202). Subsequently, cell nuclear regions (nuclear regions or second image specific regions) are extracted from the V image (step S203 (the step of extracting second image specific regions). Subsequently, information is extracted about each of the extracted nuclear regions (step S204). Nuclear regions not satisfying the predetermined shape are excluded from the nuclear region image (step S205), so that an image of section A having undergone the extraction of nuclear regions (nuclear region image) is obtained based on the HE staining. In this case, the detail of the processing in steps S201 to S205 described above is similar to that of the processing in steps S101 to S105 for the process of deriving the first region of interest.

Subsequently, the bright field image of section B as the consecutive sample is input from the microscopic image acquisition device 1A through the communication I/F 24 (step S206 (third and fourth input steps)). The bright field image of section B is then subjected to normalization and RGB decomposition (step S207).

Figure 9A:
FIG. 9A is a view showing an example of image processing in step S208 of FIG. 8.
Figure 9B:
FIG. 9B is a view showing an example of image processing in step S208 of FIG. 8.
Figure 9C:
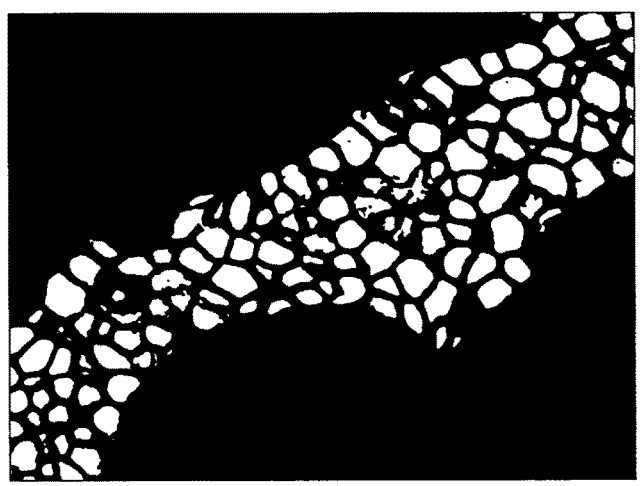
FIG. 9C is a view showing an example of image processing in step S208 of FIG. 8.

Subsequently, nuclear regions stained blue by the HE staining are extracted as fourth image specific regions from the image (B image) obtained by the extraction of the blue component from the bright field image of section B (step S208 (the step of extracting fourth image specific regions). Any method may be used to extract nuclear regions from the B image. For example, the bright field image (FIG. 9A) of section B is subjected to RGB decomposition, and each pixel value in the B image (FIG. 9B) obtained as a monochrome image by conversion is binarized using a predetermined threshold. In this regard, the threshold is appropriately changed depending on the image acquiring conditions, the staining method, the tissue section thickness, or other factors. In step S208, noise processing is further performed as in step S103. In the noise processing, regions that are determined not to be cell nuclei based on feature values such as the size and shape of the extracted nuclear regions may be excluded as in the processing of step S105 for the process of deriving the first region of interest. FIG. 9C shows an image obtained by a process that includes binarizing the image of FIG. 9B with an intensity threshold of 160, further performing noise processing and black and white reversal, and then excluding regions with an area of 20,000 pixels or more. An image having undergone the extraction of nuclear regions of section B (nuclear region image) is obtained by the processing of step S208.

Figure 10A:
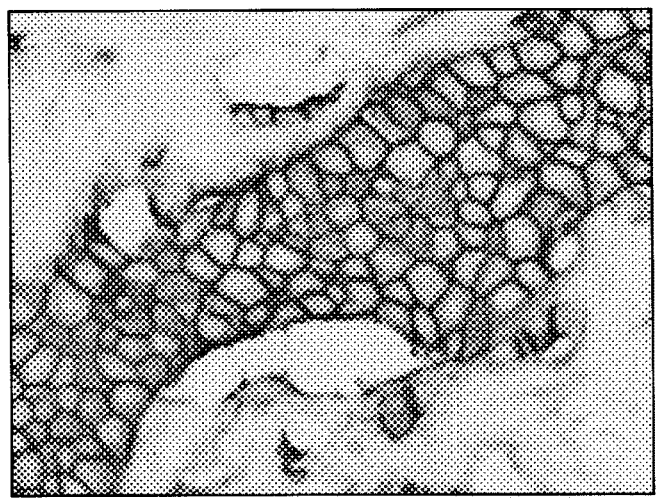
FIG. 10A is a view showing an example of image processing in step S209 of FIG. 8.

Subsequently, a region of interest of section B (a region surrounded by the cell membrane, which is a region expressing HER2, the specific protein in the embodiment) is extracted based on DAB staining from the image (R image) obtained by the extraction of the red component from the bright field image of section B (step S209 (the step of extracting a consecutive sample region of interest)). In step S209, for example, each pixel value in the R image obtained as a monochrome image by conversion as shown in FIG. 10A is binarized using a predetermined threshold. In this regard, the threshold is appropriately changed depending on the image acquiring conditions, the staining method, the tissue section thickness, or other factors. Subsequently, noise processing is performed as in step S103. In the noise processing, some regions may be excluded from the extracted regions if they have a relatively small area and can be assumed to be cells existing alone away from other cells.

Figure 10B:
FIG. 10B is a view showing an example of image processing in step S209 of FIG. 8.

FIG. 10B shows an image obtained by a process that includes binarizing the image of FIG. 10A with an intensity threshold of 180, further performing noise processing and black and white reversal, and then excluding very small regions with an area of 5,000 pixels or less. An image having a region of interest extracted based on DAB staining from section B (DAB-ROI image) is obtained by the processing of step S209.

After the processing of steps S205 and S208, pattern matching (step S210) is performed between the nuclear region image of section A (FIG. 6C) obtained in step S205 and the nuclear region image of section B (FIG. 9C) obtained in step S208. Specifically, for example, a deformed image is produced by deforming the nuclear region image of section B by any of various methods (such as movement, rotation, enlargement, and reduction) and then superimposed on the nuclear region image of section A. The degree of matching between the shapes of the nuclear regions of the two superimposed images is calculated by any method and then used to find the deformed image with the maximum degree of matching.

Figure 11A:
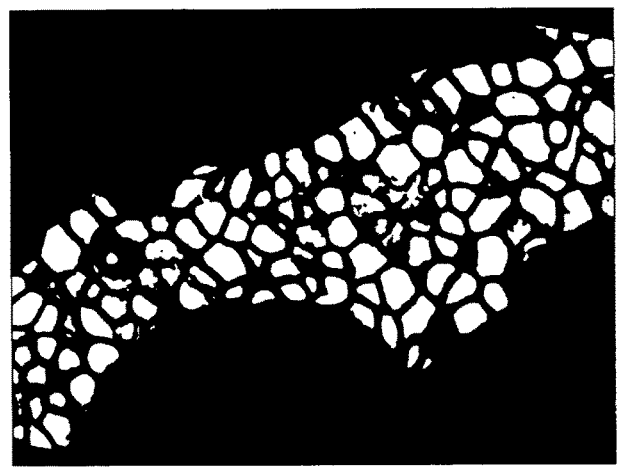
FIG. 11A is a view showing an example of image processing in steps S210 to S212 of FIG. 8.

For example, the pattern matching between the nuclear region image of section A shown in FIG. 6C and the nuclear region image of section B shown in FIG. 9C includes producing a deformed image by rotating the image of FIG. 9C clockwise by 10 degrees and further enlarging the image by 110% in the vertical direction; and superimposing the deformed image on the image of FIG. 6C, so that as shown in FIG. 11A, the shapes of the nuclear regions in the two images match best with each other and that the maximum degree of matching is achieved. In this process, the deformation parameters for the deformed image (such as the movement distance, the rotation angle, and the magnification for the production of the deformed image from the nuclear region image of section B) are used as "correction values."

Figure 11B:
FIG. 11B is a view showing an example of image processing in steps S210 to S212 of FIG. 8.
Figure 11C:
FIG. 11C is a view showing an example of image processing in steps S210 to S212 of FIG. 8.

Subsequently, the DAB-ROI image produced in step S209 is deformed using the correction values (step S211), and the deformed image is superimposed on the nuclear region image of section A (FIG. 6C). In some cases, the deformation using the correction values causes a region having no DAB-ROI image data to occur on the nuclear region image of section A. In such cases, correction is performed by any method based on adjacent image data to derive a region of interest of section A (step S212). For example, when the DAB-ROI image of FIG. 10B is deformed by 10-degree clockwise rotation and 110% enlargement in the vertical direction, the consecutive sample region of interest is partially lost due to no image data on the lower left side as shown in FIG. 11B. However, a region of interest as shown in FIG. 11C can be derived when correction for extending the consecutive sample region of interest is performed based on the image pattern around the lost portion. The control unit 21 analyzes the number of bright fluorescent spots in the region of interest derived by the processing described above and evaluates the expression of the specific protein.

In this process, section C that is in contact with the surface of section A opposite to its surface in contact with section B may be further used as a consecutive sample. Specifically, a region of interest is derived by performing the processing in the flowchart of FIG. 8 in a similar manner using each of sections B and C. The two regions of interest obtained based on sections B and C are then averaged as a region of interest of section A. It is preferable to average the regions of interest obtained using, as consecutive samples, two sections between which section A to be observed is located, because the averaging makes it possible to obtain a more accurate region of interest.

[Process of Deriving Third Region of Interest]

In the process of deriving a third region of interest, the image processor 2A derives a region of interest, based on nuclear regions, which are extracted based on HE staining, and based on bright fluorescent spots indicating the expression of the biological material. Hereinafter, the process of deriving a third region of interest will be described mainly with respect to its features different from those of the process of deriving the first region of interest, while a description of common features will be omitted.

Figure 12:
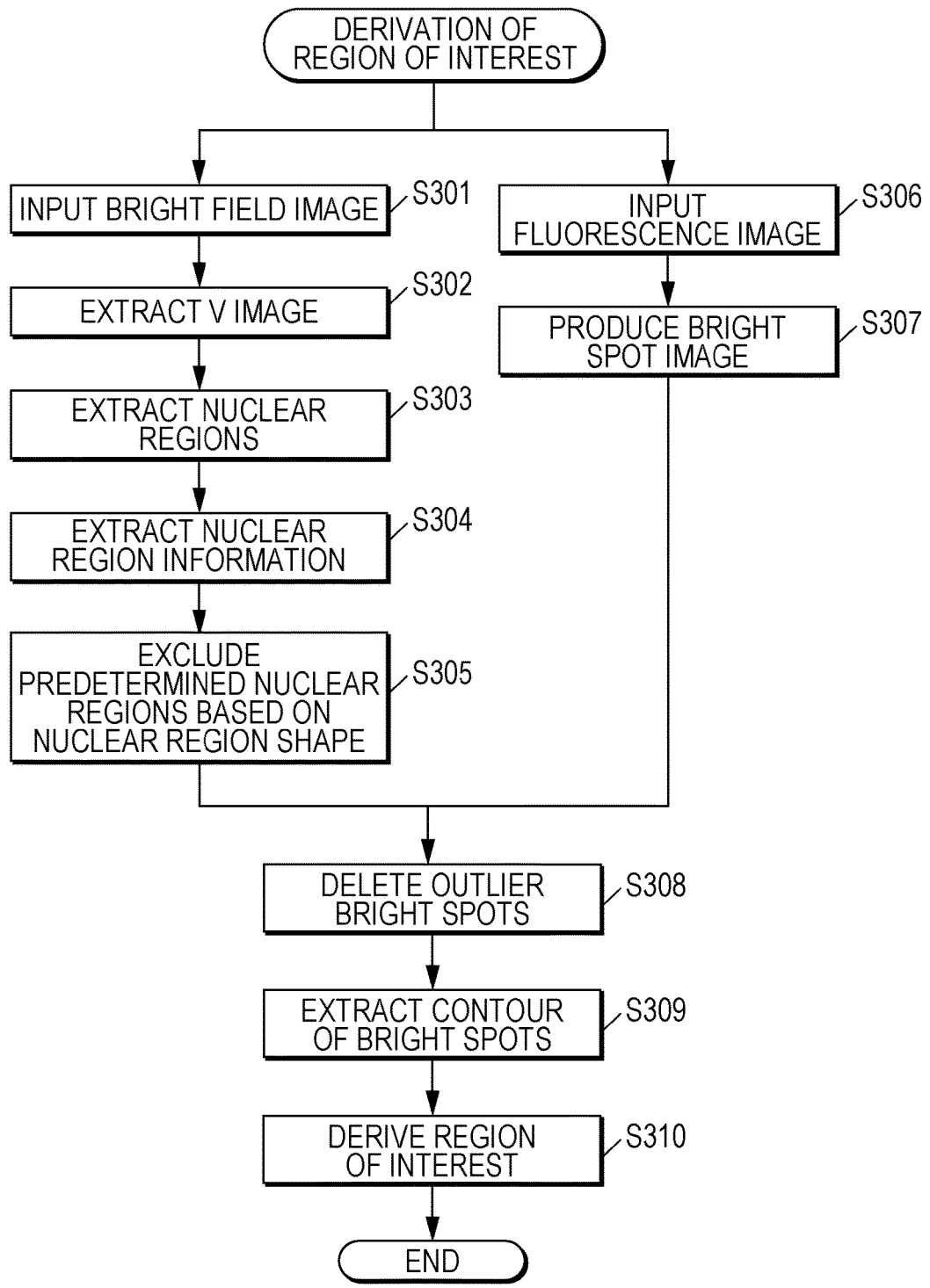
FIG. 12 is a flowchart illustrating a process of deriving a third region of interest, which is executed by the control unit shown in FIG. 2.

Firstly, using the microscopic image acquisition device 1A, the operator acquires a bright field image and a fluorescence image by the same procedures as the procedures (a1) to (a5) for acquiring the bright field image and the fluorescence image in the process of deriving the first region of interest. FIG. 12 is a flowchart illustrating the process of deriving a third region of interest in the embodiment. The third image analysis illustrated in FIG. 12 is executed by cooperation of the control unit 21 and programs stored in the storage unit 25.

Firstly, the bright field image is input from the microscopic image acquisition device 1A through the communication I/F 24 (step S301 (second input step)). The bright field image is then subjected to normalization and HSV decomposition so that the V image is extracted (step S302). Subsequently, an image (nuclear region image) is obtained by extracting cell nuclear regions (nuclear regions or second image specific regions) from the V image (step S303 (the step of extracting second image specific regions). Subsequently, information is extracted about each of the extracted nuclear regions (step S304). Nuclear regions not satisfying the predetermined shape are excluded from the nuclear region image (step S305), so that an image having undergone the extraction of cell nuclear regions (nuclear region image) is obtained based on the HE staining of the sample. In this case, the detail of the processing insteps S301 to S305 described above is similar to that of the processing in steps S101 to S105 for the process of deriving the first region of interest.

Subsequently, the fluorescence image (first image) is input from the microscopic image acquisition device 1A through the communication I/F 24 (step S306 (first input step)). A bright spot image is then produced by extracting bright fluorescent spots from the fluorescence image (step S307). Any method may be used to extract bright fluorescent spots. For example, high-pass filter processing is performed depending on the size of bright fluorescent spots so that bright fluorescent spots are extracted from the fluorescence image such as that shown in FIG. 13A. For example, when the fluorescent particles used in the first staining reagent have an average diameter corresponding to 10 pixels, a high-pass filter with a radius of 5 pixels may be used to extract only bright fluorescent spots for an image. Subsequently, a binary image is produced using a predetermined threshold, while bright fluorescent spots are extracted.

Figure 13A:
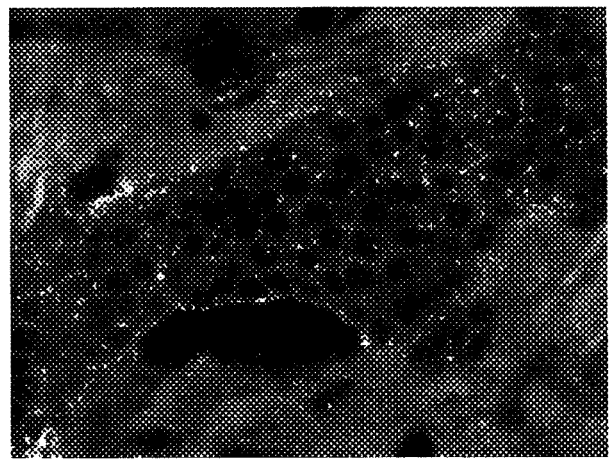
FIG. 13A is a view showing an example of image processing in steps S306 to S308 of FIG. 12.
Figure 13B:
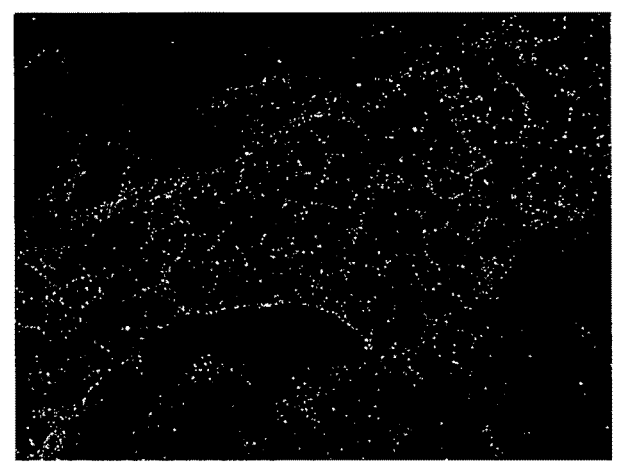
FIG. 13B is a view showing an example of image processing in steps S306 to S308 of FIG. 12.

FIG. 13B shows an exemplary image having bright fluorescent spots extracted by performing high-pass filter processing on the fluorescence image of FIG. 13A to emphasize edges and then binarizing each pixel value with a predetermined threshold.

Figure 13C:
FIG. 13C is a view showing an example of image processing in steps S306 to S308 of FIG. 12.

After the processing of steps S305 and S307, the nuclear region image and the bright spot image are superimposed, in which bright fluorescent spots the distance of which from the nuclear regions extracted in step S305 is equal to or more than a predetermined distance are excluded as being outlier bright spots (step S308). Outlier bright spots may be defined in any way. For example, the distance from each bright fluorescent spot to the closest nuclear region is calculated on the image formed by superimposing the nuclear region image and the bright spot image, and bright fluorescent spots calculated distances of which are equal to or more than a predetermined value are determined to be outlier bright spots. The predetermined distance may be freely selected depending on the average diameter of the nuclear regions or the sample type. For example, the average of the diameters of the nuclear regions, which are calculated from the nuclear region image such as that shown in FIG. 7A, is calculated and used as the predetermined distance. Such outlier bright spots may be assumed to be noise outside cells containing nuclei extracted in step S305. FIG. 13C shows an exemplary image produced when bright fluorescent spots the distance of which from the closest nuclear region is at least 50 pixels (the average diameter of the nuclear regions) are deleted as outlier bright spots from the bright spot image of FIG. 13B.

Subsequently, the contour surrounding the bright fluorescent spots is extracted (step S309) in the bright spot image obtained by the deletion of the outlier bright spots, and the inside of the extracted contour is derived as a region of interest (step S310). Any method may be used to extract the contour. For example, a technique may be used in which a known dynamic contour extraction algorithm such as SNAKES model is executed to calculate a closed curve along the bright fluorescent spots. Specifically, the technique using SNAKES model includes selecting a plurality of candidate spots in the image from which the contour is to be extracted; calculating, with respect to the candidate spots, internal energy for defining the smoothness of the contour, image energy designed in such a way that the energy at the region boundary reaches the minimum, and external energy designed in such a way that the region is expanded from the initial region; and dynamically determining the contour by controlling the candidate spots in such away that the sum of the respective energy values becomes minimal. Alternatively, for example, the convex hull of bright fluorescent spots may be calculated as the contour.

Figure 14A:
FIG. 14A is a view showing an example of image processing in steps S309 to S310 of FIG. 12.
Figure 14B:
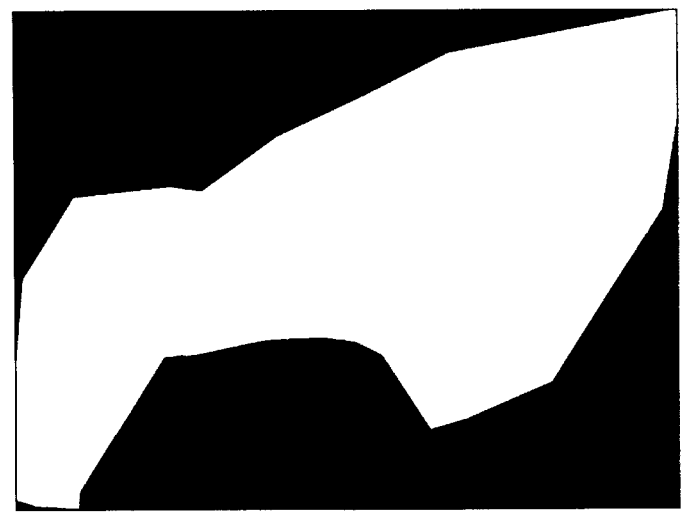
FIG. 14B is a view showing an example of image processing in steps S309 to S310 of FIG. 12.

The processing of step S310 extracts the contour such as that shown in FIG. 14A from the bright spot image such as that shown in FIG. 13C to derive the inner region of the contour as a region of interest as shown in FIG. 14B. The control unit 21 analyzes the number of bright fluorescent spots in the region of interest derived by the processing described above and evaluates the expression of the specific protein.

The processes of deriving the first to third regions of interest described above allow automatic derivation of regions of interest from a tissue section image or images. Such automatic derivation reduces the labor of the operator and eliminates operator-to-operator variation.

In addition, the tissue section to be observed for quantification of a specific protein is not stained by any technique (such as the DAB method) interfering with the staining technique for quantification of the specific protein (such as immunohistochemical staining with a fluorescent dye). This increases the accuracy of quantification of the specific protein.

In addition, whether the extracted nuclear regions (specific regions) should be used to derive a region of interest is determined based on the shape, density, size, distribution (such as whether the nuclear regions are outlier nuclei away from other cell nuclei), or other features of nuclear regions. This makes it possible to efficiently extract cells having features suitable for quantification of a specific protein and to use such cells for the derivation of a region of interest.

In the process of deriving the second region of interest, the region of interest is derived based on a DAB-stained image of an adjacent tissue section, which shows cell regions expressing a specific protein. This makes it possible to extract, as the region of interest, a cell region expressing the specific protein, and also makes it possible to efficiently detect a cancer region and the expression of the specific protein in the cancer region.

In addition, the image mismatch is corrected based on nuclear region pattern matching between consecutive tissue sections. Such correction makes it possible to accurately derive a region of interest of the tissue section as the observation object.

In the process of deriving the second region of interest, two tissue sections between which the tissue section as the observation object is located can be used as consecutive samples. In this case, a region of interest of the tissue section as the observation object can be determined as the average of regions of interest derived from DAB-ROI images of the respective consecutive samples, which is preferred.

In the process of deriving the third region of interest, the region of interest is derived based on the positions of nuclear regions and the positions of bright fluorescent spots indicating the expression of a specific protein. This makes it possible to efficiently extract a region of interest at or near a cell region expressing the specific protein and to efficiently detect a cancer region and the expression of the specific protein in the cancer region.

It will be understood that the features of the embodiment described above are mere preferred examples of the present invention and are not intended to limit the present invention. For example, the feature values of cells, the threshold for binarization, the distance, and the area used in the image processing according to the present invention may be appropriately changed depending on the imaging conditions in the microscopic image acquisition device 1A, the tissue sample, the staining reagent, the specific protein, the staining conditions, or other conditions.

The embodiment described above shows H staining and HE staining as examples of the staining method for extracting cell nuclear regions. It will be understood that these nucleus-extracting methods are not limiting and that any other known staining methods may be used, such as DAPI staining. Alternatively, in the processes of deriving the first and third regions of interest, the region of interest may be derived based on cell regions that are extracted based on, for example, self-fluorescence. Alternatively, in the process of deriving the second region of interest, pattern matching may be performed on cell regions extracted from two consecutive tissue sections, respectively. The type of the image to be acquired should be changed depending on the staining reagent used. For example, in the embodiment of the process of deriving the second region of interest, the specific protein in section B is stained by DAB method while cell nuclei in section B are stained with an HE staining reagent, and therefore the bright field image acquired in the procedure (b7) serves as both of a third image indicating the expression of the specific protein and a fourth image showing the morphology of specific regions. Alternatively, for example, the fluorescence image of section B may be acquired as one of the third and fourth images. In such a case, similarly to the procedures (b4) and (b5), the fluorescence image of section B may be acquired in the same area (the same field of view) as the bright field image of section B.

In the process of deriving the third region of interest, a dilation ratio may also be selected depending on the area of the region where bright fluorescent spots are found in the bright spot image formed in step S307, and the nuclear regions extracted in step S305 may be subjected to dilation using the dilation ratio when the region of interest is obtained. In addition, for example, the nuclear regions inside the contour of the bright fluorescent spots extracted in step S309 may also be subjected to dilation using a dilation ratio selected based on the contour of the bright fluorescent spots, when the region of interest is obtained.

In the embodiment described above, HER2 protein in breast cancer is shown as an example of the specific protein, which is not intended to be limiting. When the fluorescence image is acquired, any different biological material-recognizing component may be used, depending on the type of the lesion (cancer) to be diagnosed, so that feature values quantitatively indicating the expression level of the specific protein can be provided, depending on the lesion type, to doctors.

The above description shows examples where an HDD and a nonvolatile semiconductor memory are used as computer readable media for the program of the present invention. It will be understood that these examples are not limiting. Any other computer readable media may be used, such as portable recording media including CD-ROM. Carrier waves may also be used as media for providing the program data of the present invention via communication lines.

Moreover, the detailed configuration and operation of each unit in the pathological diagnosis support system 100 may also be changed as appropriate without departing from the gist of the present invention.

INDUSTRIAL APPLICABILITY

The present invention has features that make it possible to automatically derive, from an image of a tissue section, a region of interest for the analysis of the expression level of a specific biological material. The present invention makes it possible to reduce the labor of the operator and to prevent operator-to-operator variation and thus is particularly suitable for use in obtaining high-accuracy diagnostic information.

REFERENCE SIGNS LIST

100 Pathological diagnosis support system
1A Microscopic image acquisition device
2A Image processor
21 Control unit
22 Operation unit
23 Display unit
24 Communication I/F
25 Storage unit
26 Bus
3A Cable

The invention claimed is:

1. An image processor configured to quantify a specific biological material in a region of interest of a sample stained with a first staining reagent capable of staining the specific biological material and stained with a second staining reagent capable of staining a specific region of a cell without interfering with staining with the first staining reagent, the image processor comprising:
    first input means configured to input a first image that shows a position of expression of the biological material stained with the first staining reagent;
    second input means configured to input a second image that is acquired in the same field of view as the first image and shows a morphology of the specific region of the cell stained with the second staining reagent;
    second image specific region extraction means configured to extract, as a second image specific region, the specific region from the second image;
    derivation means configured to derive the region of interest based on at least the second image having undergone extraction of the specific region among the first image and the second image having undergone extraction of the specific region; and
    density calculation means configured to calculate a density of the specific region,
    wherein the derivation means is configured to perform dilation for dilating the specific region and to derive the dilated specific region as the region of interest, and
    wherein the derivation means is configured to determine a dilation ratio for the dilation based on the density.

2. The image processor according to claim 1, wherein the derivation means is configured to determine whether the specific region is necessary for derivation of the region of interest, based on a shape of the specific region, and to derive the region of interest by the dilation of the specific region that is determined to be necessary for derivation of the region of interest.

3. The image processor according to claim 2, wherein the derivation means is configured to determine that the specific region a distance of which from another specific region closest to the specific region is at most a predetermined distance is necessary for derivation of the region of interest.

4. The image processor according to claim 2, further comprising
    density calculation means configured to calculate a density of the specific region, wherein
    the derivation means is configured to determine a dilation ratio for the dilation based on the density.

5. The image processor according to claim 2, further comprising
    area calculation means configured to calculate an area of the specific region, wherein
    the derivation means is configured to determine a dilation ratio for the dilation based on the area.

6. The image processor according to claim 1, wherein the derivation means is configured to determine that the specific region a distance of which from another specific region closest to the specific region is at most a predetermined distance is necessary for derivation of the region of interest.

7. The image processor according to claim 6, further comprising
density calculation means configured to calculate a density of the specific region, wherein
the derivation means is configured to determine a dilation ratio for the dilation based on the density.

8. The image processor according to claim 1, further comprising
area calculation means configured to calculate an area of the specific region, wherein
the derivation means is configured to determine a dilation ratio for the dilation based on the area.

9. The image processor according to claim 1, wherein the sample is a tissue section sampled from a tissue, the image processor further comprising:
third input means configured to input a third image that allows a region of expression of the biological material to be extracted from a consecutive sample or samples stained to allow extraction of the region of expression of the biological material and the specific region of the cell, wherein the consecutive sample or samples are a tissue section or sections consecutive to the tissue section;
consecutive sample region-of-interest extraction means configured to extract, as a consecutive sample region of interest, the region of expression of the biological material from the third image;
fourth input means configured to input a fourth image showing a morphology of the specific region in the consecutive sample or samples; and
fourth image specific region extraction means configured to extract, as a fourth image specific region, the specific region in the consecutive sample or samples from the fourth image, wherein
the derivation means is configured to derive a region of interest of the sample from the consecutive sample region of interest based on shapes of the second image specific region and the fourth image specific region.

10. The image processor according to claim 9, further comprising
correction value calculation means configured to perform pattern matching between the second image specific region and the fourth image specific region after deformation of the second image or the fourth image and to calculate, as a correction value, a deformation parameter with which a degree of matching between the second image specific region and the fourth image specific region reaches a maximum, wherein
the derivation means is configured to derive a region of interest of the sample by deforming the consecutive sample region of interest based on the correction value.

11. The image processor according to claim 10, wherein the correction value includes a value for parallel translation and/or rotational transfer.

12. The image processor according to claim 10, wherein the correction value includes a value for enlargement or reduction.

13. The image processor according to claim 9, wherein the consecutive samples are two tissue sections between which the sample is located.

14. The image processor according to claim 1, wherein the derivation means is configured to derive a region of interest based on the second image having undergone extraction of the specific region and based on the first image showing the position of expression of the biological material.

15. The image processor according to claim 14, wherein the derivation means is configured to calculate a distance from each position of expression of the biological material to the specific region closest to each position in an image obtained by superimposing the second image having undergone extraction of the specific region on the first image showing the position of expression of the biological material, and also configured to derive, as a region of interest, an inside of a contour linking outer borders of positions of expression of the biological material with the calculated distance being at most a predetermined distance.

16. The image processor according to claim 15, wherein the predetermined distance is determined based on a size of the specific region.

17. An image processing method for quantifying a specific biological material in a region of interest of a sample stained with a first staining reagent capable of staining the specific biological material and stained with a second staining reagent capable of staining a specific region of a cell without interfering with staining with the first staining reagent, the method comprising:
a first input step of inputting a first image that shows a position of expression of the biological material stained with the first staining reagent;
a second input step of inputting a second image that is acquired in the same field of view as the first image and shows a morphology of the specific region of the cell stained with the second staining reagent;
a second image specific region extraction step of extracting the specific region from the second image; and
a derivation step of deriving the region of interest based on at least the second image having undergone extraction of the specific region among the first image and the second image having undergone extraction of the specific region; and
a density calculation step to calculate a density of the specific region,
wherein the derivation step performs dilation for dilating the specific region and derives the dilated specific region as the region of interest, and
wherein the derivation step determines a dilation ratio for the dilation based on the density.

18. A non-transitory recording medium storing a computer readable program for causing a computer to quantify a specific biological material in a region of interest of a sample stained with a first staining reagent capable of staining the specific biological material and stained with a second staining reagent capable of staining a specific region of a cell without interfering with staining with the first staining reagent, the program causing the computer to function as:
first input means for inputting a first image that shows a position of expression of the biological material stained with the first staining reagent;
second input means for inputting a second image that is acquired in the same field of view as the first image and shows a morphology of the specific region of the cell stained with the second staining reagent;
second image specific region extraction means for extracting the specific region from the second image; and
derivation means for deriving the region of interest based on at least the second image having undergone extraction of the specific region among the first image and the second image having undergone extraction of the specific region; and
density calculation means configured to calculate a density of the specific region, wherein the derivation means is configured to perform dilation for dilating the specific region and to derive the dilated specific region as the region of interest, and
wherein the derivation means is configured to determine a dilation ratio for the dilation based on the density.

* * * * *